United States Patent [19]

ter Huurne et al.

[11] Patent Number: 5,882,655
[45] Date of Patent: Mar. 16, 1999

[54] *SERPULINA HYODYSENTERIAE* VACCINE COMPRISING A HYGENE MUTANT

[75] Inventors: Agnes ter Huurne; Susie Jane Muir, both of Weesp, Netherlands

[73] Assignee: American Cyanamid Company, Madison, N.J.

[21] Appl. No.: 950,433

[22] Filed: Oct. 15, 1997

Related U.S. Application Data

[63] Continuation of Ser. No. 461,748, Jun. 5, 1995, abandoned, which is a continuation of Ser. No. 194,127, Feb. 9, 1994, abandoned, which is a continuation of Ser. No. 996,197, Dec. 23, 1992, abandoned.

[30] Foreign Application Priority Data

Dec. 23, 1991 [NL] Netherlands ............... 91203384.2

[51] Int. Cl.⁶ ............... A61K 39/00; A61K 39/002
[52] U.S. Cl. ............... 424/262.1; 424/92; 424/16; 435/6; 435/69.3
[58] Field of Search ............... 424/16, 92, 262.1; 435/69.3, 6

[56] References Cited

U.S. PATENT DOCUMENTS

| | | | |
|---|---|---|---|
| 4,152,413 | 5/1979 | Goodnow | 424/16 |
| 4,152,415 | 5/1979 | Harris et al. | 424/16 |
| 4,203,968 | 5/1980 | Harris et al. | 424/92 |
| 4,748,019 | 5/1988 | Lysono | 424/92 |
| 4,789,544 | 12/1988 | Nelson et al. | 424/92 |
| 5,017,478 | 5/1991 | Cashion et al. | 435/69.1 |
| 5,176,910 | 1/1993 | McCaman et al. | 424/92 |
| 5,281,416 | 1/1994 | Coloe | 424/92 |
| 5,364,774 | 11/1994 | Muir et al. | 435/69.3 |
| 5,698,394 | 12/1997 | Deihamel et al. | 435/6 |
| 7,996,197 | 12/1992 | ter Huurne et al. | 424/265.1 |
| 8,194,127 | 2/1994 | ter Huurne et al. | 424/265.1 |

OTHER PUBLICATIONS

Lysons et al, Clin & Molecular Aspects of Anaerobes, 1990 vol. 25, pp. 147–151.
Muir et al, Infect & Immunity, Feb. 1992, pp. 529–535 vol. 60(2).
M P Searce, U embl 143–89 Sequence Search, Result #1, Submission date Aug. 28, 1991.
Sambrook et al, Molecular Cloning, Cold Spring Harbor Laboratory Press, 1989, Chapter 15.
Lemcke et al, J. Med. Microbiol., vol. 15, pp. 205–214, 1982.
Goebel et al, J Bact., Sep. 1982, pp. 1290–1298, vol. 151(3).
Kent et al, J. Med. Microbiol, vol. 27, pp. 215–224, 1988.
Goebel et al, Genetic manipulation: impact on Man & Society, 1983.
Lysons et al, J. Med. Microbiol, vol. 34, 1991, pp. 97–102.
Lysons et al, Clin. Molec. Aspects of Anaerobes, 1990, pp. 147–151.
Muir et al. Infect. Immun. 001.60 pp. 529–535 (1992).
Goebel et al in Genetic Manipulation: Impact on Man and Society (PAP. COGENE Symp. Meeting date 1983) pp. 29–42 edited by W. Arbes et al., ICSU Press Cambridge.
Sambrook et al Molecular Cloning: A Laboratory Manual 2nd Edition, cold Spring Harbor Laboratory CSH; NY (1989) pp.
R.J. Lysons, et al, "A Cytotoxic Haemolysin from Treponema Hyodysenteriae: A Virulence Factor for Swine Dysentery", *Clinical and Molecular Aspects of Anaerobes*, 25, (1990) pp. 147–151.
K.A. Kent, et al, "Production, Purification and Molecular Weight Determination of the Haemolysin of Treponema Hyodysenteriae", *Med. Microbiology*, vol. 27 (1988), pp. 215–224.
Huurne, et al, "Inactivation of Serpula (Treponema) Hyodysenteriae Hemolysin Gene by Homologous Recombination: Importance of the Hemolysin in Pathogenesis of S. Hyodysenteriae in Mice", *FEMS Microbiology letters*, 92 (1992) pp. 109–114.

*Primary Examiner*—James C. Housel
*Assistant Examiner*—Ginny Allen Portner
*Attorney, Agent, or Firm*—Stevens, Davis, Miller & Mosher, L.L.P.

[57] ABSTRACT

According to the present invention a vaccine can be prepared containing a mutant *Serpulina hyodysenteriae* which is defective in its production of biologically active hemolysin. The mutation by which *Serpulina hyodysenteriae* is made defective in its production of hemolytically active hemolysin is established by means of genetical engineering techniques. Such mutations comprise e.g. deletion of part or the entire gene coding for hemolysin and/or nucleotide sequences controling the production of hemolysin, or insertion of an extra nucleotide or polynucleotide into the gene encoding hemolysin and/or the nucleotide sequences controling the production of hemolysin, or a combination of said deletion and insertion. These vaccines are useful in the prevention of Serpulina infections in susceptible animals such as swine.

9 Claims, 1 Drawing Sheet

SERPULINA HYODYSENTERIAE VACCINE COMPRISING A HYGENE MUTANT

This application is a continuation of application Ser. No. 08/461,748, filed Jun. 5, 1995, now abandoned, which is a continuation of application Ser. No. 08/194,127, filed Feb. 9, 1994, now abandoned, which is a continuation of application Ser. No. 07/996,197, filed Dec. 23, 1992, now abandoned, which claims priority to foreign application number EP 91203384.2, filed on Dec. 23, 1991 under 35 U.S.C. 119.

The present invention is concerned with a vaccine for combating Serpulina (Treponema) hyodysenteriae infection and with recombinant polynucleotides and Serpulina hyodysenteriae mutants for the preparation of such a vaccine.

Serpulina hyodysenteriae, the major etiological agent of swine dysentery is an anaerobic, β-hemolytic spirochete found in the porcine large intestine. The disease is characterized by a mucohemorrhagic diarrhoea. This seems to be associated with the extensive superficial necrosis of the luminal epithelial lining and of the crypts of Lieberkuhn.

The disease leads to dehydration, weight loss and eventually death.

This pathogen secretes hemolysin which is thought to play an essential role in the pathogenesis of the disease.

Serpulina hyodysenteriae is differentiated from the non-pathogenic, weakly β-hemolytic Serpulina innocens by its hemolytic pattern on blood agar plates, or by testing enteropathogenicity in pigs or mice.

In vivo, during the acute disease course, up till now no immunogenic response induced by hemolysin could be serologically demonstrated.

Genetic approaches to elucidate the pathogenesis of spirochaetal infections have been hampered since a genetic exchange system permitting introduction of genes into spirochetal cells was absent. No methods of transformation or general transduction have been previously described.

According to the present invention, a vaccine can be prepared containing a mutant Serpulina hyodysenteriae which is defective in its production of biologically active hemolysin.

The mutation by which Serpulina hyodysenteriae is made defective in its production of biologically active hemolysin is established by means of genetical engineering techniques. Such mutations comprise e.g. deletion of part or the entire gene encoding hemolysin and/or nucleotide sequences controling the production of hemolysin, or insertion of an extra nucleotide or polynucleotide into the gene encoding hemolysin and/or the nucleotide sequences controling the production of hemolysin, or a combination of said deletion and insertion. The extra polynucleotide used for said insertion may be either a natural polynucleotide fragment derived from Serpulina hyodysenteriae or an other organism, or an unnatural polynucleotide. The extra polynucleotide may encode a foreign protein which is expressed by the treponeme, and which might be a protein useful in the selection of the mutant and/or may be a protein characteristic for and providing immunity against Serpulina hyodysenteriae or an other organism. Alternatively, the extra nucleotide or polynucleotide may serve merely to cause a frame shift in the hemolysin gene, thus resulting in abolishment of the production of biologically active hemolysin.

Genetical engineering methods which can be applied in establishing a mutation in Serpulina hyodysenteriae that results in abolishment of hemolysin production are known in the art for analogous approaches in other organisms.

An insertion can e.g. be established by first isolating the gene encoding hemolysin of Serpulina hyodysenteriae, inserting the extra nucleotide or polynucleotide into a suitable region of the coding or controling part of said gene and transforming the Serpulina hyodysenteriae with said mutated gene, thereby establishing recombination of at least part of the isolated gene with the chromosome of Serpulina hyodysenteriae Thereafter the Serpulina hyodysenteriae bacteria wherein hemolysin production is made defective are selected.

Preferably use is made of a self-replicating construct (plasmid, phage, etc.) harboring hemolysin. Prior to insertion of the extra nucleotide or polynucleotide, the gene encoding hemolysin is treated with restriction endonuclease, preferably having specificity for a restriction site which is unique in the construct. In order to be effectively ligated into the hemolysin gene, the insert should have 3' and/or 5' ends which are complementary or which are made complementary to the two ends in the hemolysin gene at the site of insertion.

Transformation of the Serpulina hyodysenteriae can be established by electroporation.

Genetically engineered Serpulina hyodysenteriae according to the present invention is useful in the prevention or combatment of Serpulina infections in susceptible individuals, in particular in swine. To this end use is made of a vaccine which contains and immunologically adequate amount of said genetically engineered Serpulina in live or inactivated form in a suitable carrier such as a buffer or the culture medium of the cells, optionally in the presence of one or more preservative constituents. In order to prepare a vaccine form which is more stable on storage, the Serpulina may be freeze-dried, optionally in the presence of one or more stabilizing constituents. Prior to use, the freeze-dried vaccine can be reconstituted by the addition of a carrier such as water or a buffer.

The vaccine may additionally contain other immunogens for swines, such as immunogenic material characteristic of viruses such as pseudorabies virus, influenza virus, transmissible gastroenteritis virus, parvo virus, porcine endemic diarhoea virus, hog cholera virus, or immunogenic material characteristic of mycoplasms, such as Mycoplasma hyopneumoniae and Mycoplasma lyorhinis, or immunogenic material characteristic of bacteria, such as Escherichia coli, Bordetella bronchiseptica, Leptospira, Actinobaccilus pleuropneumoniae, Pasteurella multocida, Streptococcus suis.

EXAMPLE 1

CLONING OF A HEMOLYSIN GENE OF SERPULINA HYODYSENTERIAE

Materials and Methods

Bacterial and culture conditions

Figure 1:
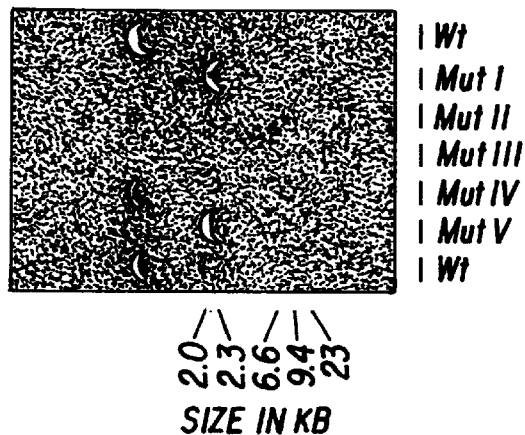
FIG. 1 shows molecular size markers in kilobase pairs (kb) are given on the right hand side.

Use was made of the Serpulina hyodysenteriae strain B204 (serotype 2) attenuated through 124 consecutive passages. The Serpulinas were grown in trypticase soy medium (Difco Laboratories, Detroit, Mich., USA) supplemented with 5% FCS (Flow) as described by Halter and Joens (1988; Infec. Immun. 56, 3152–3156). Bacterial cell pellets were washed in TE and frozen at −70° C. The plasmid pUC 19 and the phagemids pBluescript pKS+ and pSK+ (Stratagene Cloning Systems, La Jolla, Calif., USA) were utilized for the cloning procedures. *Escherichia coli* (*E. coli*) K12 strain DH5-α (Gibco BRL, Gaithersburg, Md., USA) was used as a host for these vectors.

Preparation of *Serpulina hyodysenteriae* chromosomal DNA

Molecular-grade chemicals and enzymes were from Sigma Chemical Co. (St. Louis, Mo. USA). Frozen bacterial cell pellets from 1 liter cultures were thawed in 25 ml buffer containing 100 mmol/l Tris-HCl pH 8.0, 100 mmol/l EDTA, 150 mmol/l NaCl, and 10 mg/ml lysozyme. Following a 1 hour incubation at 37° C. 0.5 ml of RNAaseA was added to the cells which were then incubated an additional 15 minutes at 70° C. Cell lysis was completed by the addition of 2.5 ml of 30% Sarkosyl, gently mixing, and incubating at 70° C. for 20 minutes followed by a 1 hour incubation at 37° C. Predigested pronase, (final concentration of 10 mg/ml) was added and incubation continued for 4 hours at 37° C. The lysate was transferred to dialysis tubing and dialyzed overnight in 6 liters of TE (10 mmol/l Tris-HCl), 1 mmol/l EDTA, pH 8.0. The DNA was then once gently extracted with TE saturated phenol, extracted with chloroform:isoamyl alcohol (24:1), dialyzed for 6 hours in TE, and ethanol precipitated. Chromosomal DNA was resuspended in TE at a concentration of 1 mg/ml. DNA prepared in this manner was used for library construction and Southern blot analysis.

Construction of *Serpulina hyodysenteriae* genomic library

Restriction enzymes, calf intestinal phosphatase, T4 DNA ligase, RNAaseA, and Klenow fragment were obtained from Boehringer Mannheim Biochemicals (Indianapolis, Ind., USA). All enzymes were used under the conditions specified by the manufacturer. Standard cloning protocols (Maniatis, T. E. F. Fritsch, and J. Sambrook. 1982. Molecular Cloning: a laboratory manual. Cold Spring Harbor Laboratory, Cold Spring Harbor, N.Y., USA) were followed for all DNA manipulations. *Serpulina hyodysenteriae* DNA was digested with the restriction enzyme MboI and ligated with T4 DNA ligase to BamHl restricted, dephosphorylated pUCI9. *E. coli* DH5-α cells were transformed with the ligation mix and recombinants screened for hemolysin production.

Screening for hemolytic clones

Recombinants were plated on trypicase soy agar containing 4% defibrinated sheep red blood cells (SRBC) (Colorado Serum Co., Denver, Colo., USA) and 100 ug/ml carbenicillin (TSA blood plates). Plates were incubated at 37° C. for 24–36 hours to detect hemolytic colonies. A single hemolytic clone, designated pSML2, was chosen for further analysis. From this clone subclones were constructed.

Southern blotting

Chromosomal DNA was digested with the restriction enzyme EcoRV, electrophoresed in a 0.8% agarose gel, and transferred to a nylon membrane. A 1.5 kbp ScaI/BamHl fragment from pJBA, the smallest subclone of pSML2 containing the active hemolysin gene, was random primer labeled with $^{32}$P (Feinborg, A. P., and B. Vogelstein. 1983. A technique for radiolabelling DNA restriction endonuclease fragments to high specificity; Anal. Biochem. 132: 6–13). Prehybridization, hybridization and washing of the membrane were at 60° C. essentially as described (Maniatis, T., E. F. Fritsch and J. Sambrook. 1982. Molecular Cloning: a laboratory manual. Cold Spring Harbor Laboratory, Cold Spring Harbor, N.Y., USA). The membrane was exposed to Kodak X-OMAT AR film at −70° C. for periods of 2 to 18 hours.

Osmotic Release of the Recombinant Hemolysin

To characterize the recombinant hemolysin, *E. coli* DH5a (pJBA) cells were subjected to osmotic shock essentially as described by Heppel (Heppel, L. A. 1967. Selective release of enzymes from bacteria. Science 156:1451–1455).

Hemolysin Assays

Aliquots of the osmotic shock supernatants were adjusted to a final concentration of 140 mmol/l NaCl and added to sheep red blood cells (SRBC) which were washed and resuspended at 10% in 140 mmol/l NaCl. The mixtures were incubated at 37° C. for one hour and the release of hemoglobin from the red cells was determined by reading the optical density of the supernatant at 540 nm.

Extraction of hemolysin from the native organism

Hemolysin was extracted from strain B204 using an RNA core extraction procedure (Kent, K. A., R. M. Lemeke, and R. J. Lysons. 1988. Production, purification and molecular weight determination of the haemolysin of *Serpulina hyodysenteriae*. J. Mod. Microbiol. 27:215–224) and concentrated.

Cytotoxity Assays

Osmotic shock supernatant from *E. coli* DH5α(pJBA), DH5α(pSML5) and DH5α(pUC1 9), and RNA core-hemolysin were filter-sterilized and added to 5×10$^4$ Chinese Hamster Ovary (CHO) cells/well as two-fold dilutions from 1:2 to 1:160. Cells were incubated at 37° C. for 24 hours in a $CO_2$ incubator and examined at various time intervals for cytopathic effect (CPE). CPE was determined by direct visual inspection of the CHO monolayer at 1, 12, and 24 hours following the addition of hemolysin to each well.

DNA Sequencing

The 1,5 kbp ScaI/BamHI insert in pJBA was subcloned into M13mp18 and M13mp19. Both strands were sequenced by dideoxynucleotide chain termination using a Sequenase kit (United State Biochemical, Cleveland, Ohio). The −40MI3 sequencing primer was used to ascertain the sites of insertion and the first one hundred bases at the 3' and 5' regions of the gene. Subsequently, based on previous sequence, oligonucleotide primers synthesized on a Cyclone Plus DNA synthesizer (Millipore Corp., Bedford, Mass., USA) were used to sequence the complete hemolysin gene.

Results

Cloning of the hemolysin gene

The plasmid vector pUC19 was utilized to prepare a library of *Serpulina hyodysenteriae* strain B 204. Plasmid DNA from the hemolytic clone, pSML2, contained a 5 kb fragment of *Serpulina hyodysenteriae*. The EcoR1 (E) subclone, pSML4, contained a 3.3 kb fragment and was as hemolytic as the parent plasmid pSML2. Digestion of pSML4 with Scal/BamHl(S:Scal) produced a 1.5 kb fragment which, when subcloned into EcoRV/BamHI restricted pBluescript phagemid pKS+ or pSK+, yielded the plasmid, pJBA, which was as hemolytic as either pSML2 or pSML4. The plasmid PJBA$^{KS}$ in *E. coli* JM105 was deposited with the Centraalbureau voor Schimmelcultures at Baarn, The Netherlands under deposit number No. 512.91.

Sequence of hemolysin

The hemolysin gene was exceptionally adenosine-plus-thymidine rich (75%) as has been reported for pathogenic and non-pathogenic strains of Serpulinas (Miao, R. M., A. H. Fieldsteel, and D. L. Harris. 1970. Genetics of Treponema: characterization of *Treponema hyodysenteriae* and its relationship to *Treponema pallidum*. Infect. Immun. 22: 736–739). The sequence is shown in SEQUENCE ID NO. 1.

EXAMPLE 2

PREPARATION OF A *SERPULINA HYODYSENTERIAE* INSERTION MUTANT

MATERIALS AND METHODS

Bacterial strains and plasmid

*Serpulina hyodysenteriae* C5 (deposited on 18 Dec. 1991 at the Centraalbureau voor Schimmelcultures at Baarn, the Netherlands under deposit number CBS 837.91) is cultured under the same conditions as described in Example 1 for the strain B204. The vector pBluescript 11 KS(+) was purchased from Stratagene (La Jolla, Calif.) and grown in *E. coli* K12 DH5α. Mice cecal contents were plated on media as described before.

Construction of a hemolysin gene containing a kanamycin resistance gene

For the construction of a hemolysin negative mutant use was made of plasmid PJBA$^{KS}$, containing the 1.5 kb Scal/BamHl fragment including the hemolysin gene (further indicated as tly) of *Serpulina hyodysenteriae* B204 with a unique Bglll site. A 1.3 kb Kanamycin Resistance GenBlock (EcoR1) (Pharmacia) was digested with the restriction enzyme BamHl and was inserted into this Bglll site. The resulting PJBA$^{KS}$ derivative was named pTly-.

Electroporation

*Serpulina hyodysenteriae* C5 was grown in 200 ml trypticase soy broth (TSB), supplemented with 5% fetal calf serum and 0.05% RNA core, for 48 hours at 42° C. under anaerobic conditions. Cells were centrifuged, washed and harvested in 50 ml of icecold 15% glycerol-272 mM sucrose, centrifuged and resuspended to $10^{10}$ cells/ml in the same medium. Aliquots were frozen and kept at −80° C. until used. 50 μl of cell suspension was mixed with 5 μg of DNA in water. Electroporation was performed with a Bio-Rad Gene Pulser with pulse controller in 0.56 mm gap cuvettes (Biotechnologies and Experimental Research Inc., San Diego, Calif.) at 0.6kV, 25 μF and 200Ω. This leads to time constants ranging from 3.5 to 4 ms. Cells were recovered in 1 ml TSB and poured onto trypticase soy agarplates, supplemented with 5% sheep blood and 400 μg of spectinomycin per ml (TSAB+). After 8 and 14 h of regeneration at 42° C. under anaerobic conditions, cells were harvested, plated onto TSAB+ agar plates supplemented with 30 or 150 μg/ml kanamycin and grown for 4 days at 42° C. under anaerobic conditions. Colonies were screened for diminished hemolysis. The electroporation experiments were carried out in duplicate.

Polymerase chain reaction

Colonies with diminished hemolysis detected after electroporation, and wildtype (Wt) *Serpulina hyodysenteriae* C5 were screened with polymerase chain reaction (PCR). DNA amplification with Taq polymerase and Taq polymerase buffer (Promega) was performed with primers corresponding to nucleotides 471–486 and 1449–1431 of the pJBA Sequence ID No. 1. This resulted in an amplified product of 0.98 kb of the tly gene including the Bglll site. For the Wt C5, 0.5 μg DNA was used. Colonies of the mutants were touched with a sterile toothpick and transferred to the PCR buffer. After the mixtures were preheated at 95° C. for 3 minutes, 35 amplification cycles were performed in a DNA Incubator Prem, as follows: 1 min at 95° C., 1 min at 40° C. and 2 min at 72° C. After the final cycle, the mixture was incubated for 10 min at 72° C. to complete the last polymerase reaction. Reaction mixtures were analyzed by agarose gel electrophoresis as described before.

Isolation of DNA and Southern blot analysis

Plasmid DNA was isolated from *E.coli* and *Serpulina hyodysenteriae* by the method of Birnboim and Doly (Nucleic Acids Research 7, 1513–1523; 1989). Chromosomal DNA of *Serpulina hyodysenteriae* was isolated by isopropanol precipitation and phenol extraction. DNA was digested with EcoRV as indicated by the supplier (BRL). EcoRI digests of pBluescript II KS(+) and a pBluescript II KS(+)/Kanamycin Resistance Genblock construct were taken as controls. Hybridization on Hybond N (Amersham) and washing was performed as described before. The 1.5 kb Scal/BamHl fragment of $PJBA^{KS}$ (Tly probe), the 1.3 kb Kanamycin Resistance Genblock (Pharmacia) (Kana probe) and the complete vector Bluescript (BS probe) were radiolabeled and used as probes.

Virulence test in mice

The mouse challenge studies were done as described before. Six week old female OF-1 mice (Iffa Credo) were kept under controlled conditions. Feed was removed 14 h before the first challenge and was withheld for 40 hours. Mice were administered two consecutive doses (24 h apart) by gastric intubation with 0.5 ml of a log-phase culture of serpulinas: $10^6$ or $10^{8\ CFU}$ *Serpulina hyodysenteriae* Wt C5, $10^6$ or $10^{8\ CFU}$ *Serpulina hyodysenteriae* C5 tly-, or $10^8$ CFU *Serpulina innocens* ATCC 29796. Three control mice were inoculated with 0.5 ml TSB. The mice were necropsied 12 days later to evaluate signs of *Serpulina hyodysenteriae* infection in the cecum: catarrhal inflammation, excess intraluminal mucus, oedema, hyperemia and atrophy. Cecal contents were cultured to assay shedding of serpulinas.

Results

Electroporation

In two separate experiments with the pTly construct, a total of 5 kanamycin resistant colonies with diminished hemolysis were recovered. In the first experiment, when cells were plated on TSAB+ plates with only 30 μg/ml kanamycin, one less hemolytic colony (MuII) was recovered among many strong hemolytic colonies. In the second experiment, when cells were plated on TSAB+ plates with 150 μg/ml kanamycin, 4 colonies with diminished hemolysis (MutII-V) were found.

Polymerase chain reaction

Upon analysis of the PCR products of *Serpulina hyodysenteriae* Wt C5 and MutI-MutV by agarose gel electrophoresis, Wt C5 and MutIV showed a fragment of only 0.98 kb, which is the expected size of the fragment of the tly gene amplified by the primers of pJBA used. MutI, MutII, MutII and MutV showed a fragment of 2.28 kb (0.98 kb of the tly gene and 1.30 kb of the kanamycin gene block) (FIG. 1; molecular size markers in kilobase pairs (kb) are given on the right hand side of this figure).

DNA isolation and Southern blot analysis

Figure 2:
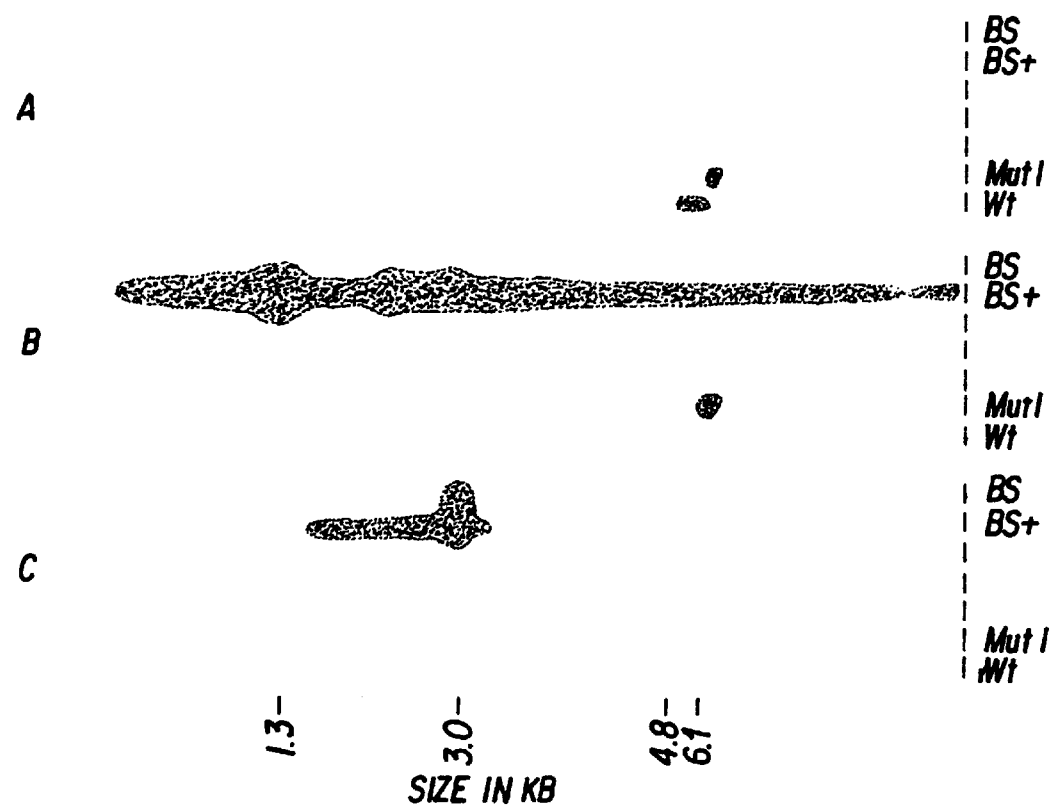
FIG. 2A is a Southern blot of Tly probe hubridized in Mutl-V strain of Serpulina hyodysenteriae.
FIG. 2B is a Southern blot of Kana probe hubridized in Mutl-V strain of Serpulina hyodysenteriae.
FIG. 2C is a Southern blot of BS probe hybridized in Mutl-V and WtC5 strain of Serpulina hyodysenteriae.

No plasmid DNA could be isolated from the mutants MutI-V. Chromosomal DNA of *Serpulina hyodysenteriae* Wt C5 and MutI-V was digested with EcoRV, blotted and hybridized with the Tly probe, Kana probe and BS probe respectively. In strain Wt C5 the Tly probe hybridized with a fragment of 4.8 kb. In MutI this probe hybridized with a fragment of 6.1 kb (i.e. 4.8 kb plus 1.3 kb kanamycin gene insertion) (FIG. 2A). Strain Wt C5 did not hybridize with the Kana probe. A fragment of 6.1 kb in MutI hybridized with the Kana probe (FIG. 2B). Neither MutI nor WtC5 hybridized with the BS probe (FIG. 2C).

Virulence test of MutI in Mice

Six groups of OF-1 mice were challenged with $10^6$ or $10^8$ CFU of *Serpulina hyodysenteriae* Wt C5, $10^6$ or $10^8$ CFU of MutI, $10^8$ CFU of Serpulina innocens ATCC 29796, or TSB (controls). Mice were killed at day 12 for evaluation of cecal lesions (catarrhal inflammation, excess intraluminal mucus, oedema, hyperemia and atrophy) and colonization by serpulinas. Cecal scores are represented in Table 1. Macroscopic cecal lesions were scored as follows: severe lesions, 3; moderate lesions, 2; mild lesions, 1; no lesions, 0. Macroscopic cecal lesions were less severe in mice infected with MutI (both inoculation doses) than in mice infected with Seruplina hyodysenteriae Wt C5. Mice infected with *Serpulina innocens* or inoculated with TSB, did not show any cecal lesions. The number of mice that were culture positive, are also shown in Table 1. In the group infected with *Serpulina innocens,* no mouse was culture positive.

TABLE 1

| group mice[e] | CFU | n[f] | group mean cecal score | number of mice lesion positive | number of mice culture positive |
|---|---|---|---|---|---|
| Wt C5 | $10^8$ | 7 | 2.42 | 7 | 7 |
| Wt C5 | $10^6$ | 6 | 1.66 | 6 | 5 |
| MutI | $10^8$ | 7 | 1.28 | 5 | 7 |
| MutI | $10^6$ | 7 | 1.00 | 5 | 4 |
| S.inno[c] | $10^8$ | 7 | 0 | 0 | 0 |
| TSB | | 3 | 0 | 0 | 0 |

[a]*Serpulina hyodysenteriae* C5 wildtype

[b]MutI = hemolysin tly-mutant of *Serpulina hyodysenteriae* C5

[c]S.inno = *Serpulina innocens* American Type culture Collection (ATCC) 29796

[d]TSB = trypticase soy broth

[e]female SPF OF-1 mice (Iffa Credo)

[f]n = number of mice per group

[g]cecal score: macroscopic cecal lesions were scored as follows: severe lesions, 3; moderate lesions, 2; mild lesions, 1; no lesions, 0.

We claim:

1. A mutant strain of *Serpulina hyodysenteriae* capable of eliciting a protective immune response against a wild-type virulent strain of *Serpulina hyodysenteriae* which mutant strain is less virulent than the wild-type strain, wherein the expression of hemolysin encoded by the chromosomal tly gene is abolished through the deletion of the entire tly gene.

2. A mutant strain of *Serpulina hyodysenteriae* capable of eliciting a protective immune response against a wild-type virulent strain of *Serpulina hyodysenteriae* which mutant strain is less virulent than the wild-type strain, said mutant strain being generated by using a genetic engineering technique comprising introducing an insertion mutation into the tly gene that results in a shift in the reading frame of the tly gene, wherein said insertion mutation is a polynucleotide coding for a selectable characteristic whereby the expression of hemolysin encoded by the chromosomal tly gene is abolished.

3. A mutant strain according to claim 2, wherein said polynucleotide is inserted in the BglII site located between nucleotides 506–511 of SEQ ID NO: 1.

4. A vaccine containing a mutant strain of *Serpulina hyodysenteriae* according to claim 1 and a suitable carrier.

5. A vaccine containing a mutant strain of *Serpulina hyodysenteriae* according to claim 2 and a suitable carrier.

6. A vaccine containing a mutant strain of *Serpulina hyodysenteriae* according to claim 3 and a suitable carrier.

7. A method for reducing the severity of a *Serpulina hyodysenteriae* infection, comprising administering to a susceptible host a vaccine according to claim 4.

8. A method for reducing the severity of a *Serpulina hyodysenteriae* infection, comprising administering to a susceptible host a vaccine according to claim 5.

9. A method for reducing the severity of a *Serpulina hyodysenteriae* infection, comprising administering to a susceptible host a vaccine according to claim 6.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 1498 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: SERPULINA HYODYSENTERIAE
( B ) STRAIN: B 204
( H ) CELL LINE: E. COLI JM105 (pJBA) [CBS 512.91]

( i x ) FEATURE:
( A ) NAME/KEY: CDS
( B ) LOCATION: 1..456
( D ) OTHER INFORMATION: /product= "UNKNOWN PROTEIN"

( i x ) FEATURE:
( A ) NAME/KEY: intron
( B ) LOCATION: 457..470

-continued ( i x ) FEATURE:
    ( A ) NAME/KEY: CDS
    ( B ) LOCATION: 471..1190
    ( D ) OTHER INFORMATION: /product= "HEMOLYSIN PROTEIN"

( i x ) FEATURE:
    ( A ) NAME/KEY: intron
    ( B ) LOCATION: 1191..1498

( x i ) SEQUENCE DESCRIPTION: SEQ ID NO:1:

```
GAT  CCT  AAT  GCT  GAT  ACT  GAT  GAA  TCT  CCT  GCT  TTA  TTG  ATT  TCT  GCT        48
Asp  Pro  Asn  Ala  Asp  Thr  Asp  Glu  Ser  Pro  Ala  Leu  Leu  Ile  Ser  Ala
 1              5                        10                       15

TCT  ATA  ACT  GAT  ACT  GAT  ACA  GTT  AAA  GTA  ATA  TTA  CAG  GCA  TTT  GCT        96
Ser  Ile  Thr  Asp  Thr  Asp  Thr  Val  Lys  Val  Ile  Leu  Gln  Ala  Phe  Ala
               20                        25                       30

GAA  GAT  GTT  ACT  GAT  GAT  ATT  TAT  ACA  ATT  GGC  GGT  AAT  TTA  TGC  TAT       144
Glu  Asp  Val  Thr  Asp  Asp  Ile  Tyr  Thr  Ile  Gly  Gly  Asn  Leu  Cys  Tyr
          35                        40                       45

ATA  AAA  GAT  TCT  ATA  TTA  TAT  ATT  TCT  GAT  AAT  TCT  AAT  GTT  ATA  GAT       192
Ile  Lys  Asp  Ser  Ile  Leu  Tyr  Ile  Ser  Asp  Asn  Ser  Asn  Val  Ile  Asp
     50                        55                       60

TCT  ATA  ATT  AAT  GGT  GAA  AAG  CCA  GCA  ACA  GCA  TTA  TCT  GCT  GAT  AAA       240
Ser  Ile  Ile  Asn  Gly  Glu  Lys  Pro  Ala  Thr  Ala  Leu  Ser  Ala  Asp  Lys
 65                       70                       75                       80

GTT  GAA  ATA  GCT  AAA  AAT  AAT  ACT  ATG  GCT  TTA  TAT  TTA  GAG  TTT  AAT       288
Val  Glu  Ile  Ala  Lys  Asn  Asn  Thr  Met  Ala  Leu  Tyr  Leu  Glu  Phe  Asn
                    85                       90                       95

TCT  AAT  TTA  TCA  TTA  TAT  GGT  ATT  GGA  GAT  GAA  TAT  ACT  GAA  ACT  TTT       336
Ser  Asn  Leu  Ser  Leu  Tyr  Gly  Ile  Gly  Asp  Glu  Tyr  Thr  Glu  Thr  Phe
               100                      105                      110

GAA  TCA  GTT  TAT  ATA  ACT  TCA  AAT  ATA  TTA  GAA  AGC  AAT  CAT  ACT  CAA       384
Glu  Ser  Val  Tyr  Ile  Thr  Ser  Asn  Ile  Leu  Glu  Ser  Asn  His  Thr  Gln
          115                      120                      125

ATG  CTT  TTA  AAA  GTA  AAT  ATG  AGA  GAT  AAA  GAA  AGA  AAT  TCT  CTT  TCT       432
Met  Leu  Leu  Lys  Val  Asn  Met  Arg  Asp  Lys  Glu  Arg  Asn  Ser  Leu  Ser
     130                      135                      140

ATA  ATA  AAA  TCT  TTC  CTT  GGA  TTA  TAATACTAAT  ATAA  ATG  CGA  TTA  GAT       482
Ile  Ile  Lys  Ser  Phe  Leu  Gly  Leu                      Met  Arg  Leu  Asp
145                      150                                 1

GAA  TAT  GTG  CAT  AGT  GAA  GGC  TAT  ACA  GAA  AGC  AGA  TCT  AAA  GCA  CAG       530
Glu  Tyr  Val  His  Ser  Glu  Gly  Tyr  Thr  Glu  Ser  Arg  Ser  Lys  Ala  Gln
 5                        10                       15                       20

GAT  ATA  ATA  CTA  GCC  GGT  TGT  GTT  TTT  GTT  AAT  GGA  GTA  AAG  GTA  ACT       578
Asp  Ile  Ile  Leu  Ala  Gly  Cys  Val  Phe  Val  Asn  Gly  Val  Lys  Val  Thr
                    25                       30                       35

TCT  AAG  GCT  CAT  AAA  ATA  AAA  GAT  ACT  GAT  AAT  ATA  GAA  GTT  GTT  CAG       626
Ser  Lys  Ala  His  Lys  Ile  Lys  Asp  Thr  Asp  Asn  Ile  Glu  Val  Val  Gln
               40                       45                       50

AAT  ATA  AAA  TAT  GTA  TCA  AGA  GCT  GGA  GAA  AAA  TTA  GAA  AAG  GCG  TTT       674
Asn  Ile  Lys  Tyr  Val  Ser  Arg  Ala  Gly  Glu  Lys  Leu  Glu  Lys  Ala  Phe
          55                       60                       65

GTA  GAA  TTT  GGA  ATA  TCT  GTA  GAA  AAT  AAA  ATA  TGT  TTA  GAT  ATA  GGA       722
Val  Glu  Phe  Gly  Ile  Ser  Val  Glu  Asn  Lys  Ile  Cys  Leu  Asp  Ile  Gly
     70                       75                       80

GCT  TCT  ACA  GGA  GGA  TTT  ACA  GAT  TGT  CGT  CTT  AAG  CAT  GGT  GCT  AAA       770
Ala  Ser  Thr  Gly  Gly  Phe  Thr  Asp  Cys  Arg  Leu  Lys  His  Gly  Ala  Lys
 85                       90                       95                      100

AAA  GTT  TAT  GCT  CTT  GAT  GTA  GGA  CAT  AAT  CAG  CTA  GTT  TAT  AAA  CTT       818
Lys  Val  Tyr  Ala  Leu  Asp  Val  Gly  His  Asn  Gln  Leu  Val  Tyr  Lys  Leu
                    105                      110                      115

CGT  AAT  GAT  AAT  AGG  GTA  GTG  TCA  ATA  GAA  GAT  TTC  AAT  GCC  AAA  GAT       866
```

| | | | | | | | | | | | | | | | | |
|---|---|---|---|---|---|---|---|---|---|---|---|---|---|---|---|---|
| Arg | Asn | Asp | Asn | Arg | Val | Val | Ser | Ile | Glu | Asp | Phe | Asn | Ala | Lys | Asp | |
| | | | 120 | | | | 125 | | | | | 130 | | | | |
| ATA | AAT | AAA | GAA | ATG | TTC | AAT | GAT | GAA | ATC | CCA | TCT | GTA | ATA | GTA | AGT | 914 |
| Ile | Asn | Lys | Glu | Met | Phe | Asn | Asp | Glu | Ile | Pro | Ser | Val | Ile | Val | Ser | |
| | | 135 | | | | | 140 | | | | | 145 | | | | |
| GAC | GTA | TCA | TTT | ATA | TCA | ATA | ACA | AAA | ATA | GCA | CCA | ATC | ATA | TTT | AAA | 962 |
| Asp | Val | Ser | Phe | Ile | Ser | Ile | Thr | Lys | Ile | Ala | Pro | Ile | Ile | Phe | Lys | |
| | 150 | | | | | 155 | | | | | 160 | | | | | |
| GAA | TTA | AAT | AAT | TTA | GAG | TTT | TGG | GTA | ACT | TTA | ATA | AAA | CCA | CAA | TTT | 1010 |
| Glu | Leu | Asn | Asn | Leu | Glu | Phe | Trp | Val | Thr | Leu | Ile | Lys | Pro | Gln | Phe | |
| 165 | | | | | 170 | | | | | 175 | | | | | 180 | |
| GAA | GCT | GAA | AGA | GGT | GAT | GTT | TCA | AAA | GGC | GGT | ATA | ATA | CGA | GAT | GAT | 1058 |
| Glu | Ala | Glu | Arg | Gly | Asp | Val | Ser | Lys | Gly | Gly | Ile | Ile | Arg | Asp | Asp | |
| | | | | 185 | | | | | 190 | | | | | 195 | | |
| ATA | CTT | AGA | GAA | AAA | ATA | TTA | AAT | AAT | GCT | ATT | TCA | AAG | ATA | ATA | GAC | 1106 |
| Ile | Leu | Arg | Glu | Lys | Ile | Leu | Asn | Asn | Ala | Ile | Ser | Lys | Ile | Ile | Asp | |
| | | | 200 | | | | | 205 | | | | | 210 | | | |
| TGC | GGA | TTT | AAA | GAA | GTT | AAT | AGA | ACC | ATC | TCT | CCT | ATA | AAA | GGT | GCT | 1154 |
| Cys | Gly | Phe | Lys | Glu | Val | Asn | Arg | Thr | Ile | Ser | Pro | Ile | Lys | Gly | Ala | |
| | | 215 | | | | | 220 | | | | | 225 | | | | |
| AAA | GGT | AAT | ATA | GAA | TAT | TTA | GCT | CAT | TTT | ATT | ATT | TAATCATTTT | | | | 1200 |
| Lys | Gly | Asn | Ile | Glu | Tyr | Leu | Ala | His | Phe | Ile | Ile | | | | | |
| | 230 | | | | | 235 | | | | | 240 | | | | | |

| | | | | | |
|---|---|---|---|---|---|
| CTATTTTATG | TGTATTTCTC | TGTTTATATA | TTTCATATTC | TTTATAGAAG | CCTTCTACAT | 1260 |
| CATTTACCAT | TAAATATCCT | TCTTCTGATA | TATCTAATGA | TTTTATTTTT | AATATTTCAT | 1320 |
| TTTCTACATT | ACTTTTATAT | TCTATGCCTA | TCATAGAACA | AATATCATTT | ATATTATATT | 1380 |
| GAAATTTTAT | TTTGTTTATA | TTTTTGAATA | AAAGTTCAGT | TTTTATTAAC | GCTTCTATTA | 1440 |
| TTATCACGAA | TTTGCTTACT | ACTTTATTAG | CATTAAAAGA | CCTTATTCTA | GAAATAGT | 1498 |

( 2 ) INFORMATION FOR SEQ ID NO:2:

( i ) SEQUENCE CHARACTERISTICS:
        ( A ) LENGTH: 152 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Asp | Pro | Asn | Ala | Asp | Thr | Asp | Glu | Ser | Pro | Ala | Leu | Leu | Ile | Ser | Ala |
| 1 | | | | 5 | | | | | 10 | | | | | 15 | |
| Ser | Ile | Thr | Asp | Thr | Asp | Thr | Val | Lys | Val | Ile | Leu | Gln | Ala | Phe | Ala |
| | | | 20 | | | | | 25 | | | | | 30 | | |
| Glu | Asp | Val | Thr | Asp | Asp | Ile | Tyr | Thr | Ile | Gly | Gly | Asn | Leu | Cys | Tyr |
| | | | 35 | | | | 40 | | | | | 45 | | | |
| Ile | Lys | Asp | Ser | Ile | Leu | Tyr | Ile | Ser | Asp | Asn | Ser | Asn | Val | Ile | Asp |
| | 50 | | | | | 55 | | | | | 60 | | | | |
| Ser | Ile | Ile | Asn | Gly | Glu | Lys | Pro | Ala | Thr | Ala | Leu | Ser | Ala | Asp | Lys |
| 65 | | | | | 70 | | | | 75 | | | | | | 80 |
| Val | Glu | Ile | Ala | Lys | Asn | Asn | Thr | Met | Ala | Leu | Tyr | Leu | Glu | Phe | Asn |
| | | | | 85 | | | | 90 | | | | | 95 | | |
| Ser | Asn | Leu | Ser | Leu | Tyr | Gly | Ile | Gly | Asp | Glu | Tyr | Thr | Glu | Thr | Phe |
| | | | | 100 | | | | 105 | | | | | 110 | | |
| Glu | Ser | Val | Tyr | Ile | Thr | Ser | Asn | Ile | Leu | Glu | Ser | Asn | His | Thr | Gln |
| | | 115 | | | | | 120 | | | | | 125 | | | |
| Met | Leu | Leu | Lys | Val | Asn | Met | Arg | Asp | Lys | Glu | Arg | Asn | Ser | Leu | Ser |
| | | 130 | | | | | 135 | | | | 140 | | | | |

```
Ile  Ile  Lys  Ser  Phe  Leu  Gly  Leu
145                 150
```

( 2 ) INFORMATION FOR SEQ ID NO:3:

( i ) SEQUENCE CHARACTERISTICS:
        ( A ) LENGTH: 240 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met  Arg  Leu  Asp  Glu  Tyr  Val  His  Ser  Glu  Gly  Tyr  Thr  Glu  Ser  Arg
 1                   5                        10                       15
Ser  Lys  Ala  Gln  Asp  Ile  Ile  Leu  Ala  Gly  Cys  Val  Phe  Val  Asn  Gly
              20                        25                       30
Val  Lys  Val  Thr  Ser  Lys  Ala  His  Lys  Ile  Lys  Asp  Thr  Asp  Asn  Ile
              35                        40                       45
Glu  Val  Val  Gln  Asn  Ile  Lys  Tyr  Val  Ser  Arg  Ala  Gly  Glu  Lys  Leu
         50                        55                  60
Glu  Lys  Ala  Phe  Val  Glu  Phe  Gly  Ile  Ser  Val  Glu  Asn  Lys  Ile  Cys
 65                        70                       75                       80
Leu  Asp  Ile  Gly  Ala  Ser  Thr  Gly  Gly  Phe  Thr  Asp  Cys  Arg  Leu  Lys
                   85                        90                       95
His  Gly  Ala  Lys  Lys  Val  Tyr  Ala  Leu  Asp  Val  Gly  His  Asn  Gln  Leu
              100                      105                     110
Val  Tyr  Lys  Leu  Arg  Asn  Asp  Asn  Arg  Val  Val  Ser  Ile  Glu  Asp  Phe
         115                      120                     125
Asn  Ala  Lys  Asp  Ile  Asn  Lys  Glu  Met  Phe  Asn  Asp  Glu  Ile  Pro  Ser
    130                      135                     140
Val  Ile  Val  Ser  Asp  Val  Ser  Phe  Ile  Ser  Ile  Thr  Lys  Ile  Ala  Pro
145                      150                     155                     160
Ile  Ile  Phe  Lys  Glu  Leu  Asn  Asn  Leu  Glu  Phe  Trp  Val  Thr  Leu  Ile
              165                     170                     175
Lys  Pro  Gln  Phe  Glu  Ala  Glu  Arg  Gly  Asp  Val  Ser  Lys  Gly  Gly  Ile
              180                     185                     190
Ile  Arg  Asp  Asp  Ile  Leu  Arg  Glu  Lys  Ile  Leu  Asn  Asn  Ala  Ile  Ser
         195                     200                     205
Lys  Ile  Ile  Asp  Cys  Gly  Phe  Lys  Glu  Val  Asn  Arg  Thr  Ile  Ser  Pro
    210                      215                     220
Ile  Lys  Gly  Ala  Lys  Gly  Asn  Ile  Glu  Tyr  Leu  Ala  His  Phe  Ile  Ile
225                      230                     235                     240
```